United States Patent
Walton et al.

(10) Patent No.: US 9,255,794 B2
(45) Date of Patent: Feb. 9, 2016

(54) MICROWAVE PROBE FOR FURNACE REFRACTORY MATERIAL

(71) Applicant: PaneraTech, Inc., Baltimore, MD (US)

(72) Inventors: Eric Walton, Columbus, OH (US); Yakup Bayram, Columbus, OH (US)

(73) Assignee: PANERATECH, INC., Chantilly, VA (US)

( * ) Notice: Subject to any disclaimer, the term of this patent is extended or adjusted under 35 U.S.C. 154(b) by 568 days.

(21) Appl. No.: 13/706,787

(22) Filed: Dec. 6, 2012

(65) Prior Publication Data

US 2013/0144554 A1   Jun. 6, 2013

Related U.S. Application Data

(60) Provisional application No. 61/567,331, filed on Dec. 6, 2011.

(51) Int. Cl.
| | | |
|---|---|---|
| *G06F 15/00* | (2006.01) | |
| *G01B 15/02* | (2006.01) | |
| *F27D 21/00* | (2006.01) | |
| *G01N 22/02* | (2006.01) | |

(52) U.S. Cl.
CPC ............. *G01B 15/02* (2013.01); *G06F 15/00* (2013.01); *F27D 21/0021* (2013.01); *G01N 22/02* (2013.01)

(58) Field of Classification Search
CPC ........ G01B 15/02; G06F 15/00; G01N 22/02; F27D 21/0021
See application file for complete search history.

(56) References Cited

U.S. PATENT DOCUMENTS

| | | |
|---|---|---|
| 3,775,765 A | 11/1973 | Di Piazza et al. |
| 4,107,244 A | 8/1978 | Ochiai et al. |
| 4,708,482 A | 11/1987 | Neiheisel |

(Continued)

FOREIGN PATENT DOCUMENTS

JP   2006153845   6/2006

OTHER PUBLICATIONS

Fleischmann, Bernard. "Non-destructive testing of refractories, especially AZS materials, with ultrasound, microwaves, and y-radiation." Glastech. Ber. Glass Sci. Technol. 68 (1995) No. 8.

(Continued)

*Primary Examiner* — Mohamed Charioui
*Assistant Examiner* — John Kuan
(74) *Attorney, Agent, or Firm* — Whiteford, Taylor & Preston, LLP; Gregory M. Stone (57) ABSTRACT

Disclosed is a system and method to aid in these inspections that avoid the disadvantages of the prior art. The system and method are operative to take thickness measurements of, and thus evaluate the condition of, materials including but not limited to refractory materials, operating in frequency bands that result in less loss than previously known technologies, and utilizing a system configuration and signal processing techniques that isolate the reflected signal of interest from other spurious antenna reflections, particularly by creating (through the configuration of the antenna assembly) a time delay between such spurious reflections and the actual reflected signal of interest, thus enabling better isolation of the signal of interest. Still further, the antenna assembly is intrinsically matched to the material to be probed, such as by impedance matching the antenna to the particular material (through knowledge of the dielectric and magnetic properties of the material to be evaluated) to even further suppress spurious reflections.

19 Claims, 8 Drawing Sheets

(56) References Cited

U.S. PATENT DOCUMENTS

| | | | |
|---|---|---|---|
| 5,212,738 A | 5/1993 | Chande et al. | |
| 5,333,493 A * | 8/1994 | Cutmore | G01N 22/04 324/640 |
| 5,363,106 A | 11/1994 | Hosoda et al. | |
| 5,504,490 A * | 4/1996 | Brendle | G01S 13/24 340/612 |
| 5,955,671 A * | 9/1999 | Gilmore | G01N 29/0681 73/597 |
| 6,198,293 B1 | 3/2001 | Woskov et al. | |
| 2002/0158368 A1 | 10/2002 | Wirth | |
| 2004/0177692 A1 | 9/2004 | Sadri et al. | |
| 2005/0133192 A1 | 6/2005 | Meszaros et al. | |
| 2008/0185903 A1 | 8/2008 | Bausov et al. | |
| 2009/0033578 A1 | 2/2009 | Martek et al. | |
| 2009/0066344 A1 | 3/2009 | Bray et al. | |
| 2009/0179152 A1 | 7/2009 | Ellison | |
| 2010/0095740 A1 | 4/2010 | Walton et al. | |
| 2010/0123467 A1 | 5/2010 | Andarawis et al. | |
| 2010/0213922 A1 | 8/2010 | Sadri et al. | |
| 2010/0265117 A1 | 10/2010 | Weiss | |

OTHER PUBLICATIONS

Fleischmann, Bernard. "Ultrasonic determination of the residual wall thickness of glass furnace refractories." Glastech. Ber. Glass Sci. Technol. 70 (1997) No. 1.

Hobson, G.S., et al. "Microwave Measurement of Furnace Wall Thickness." Microwave Conference, 17th European (Sep. 7-11, 1987. pp. 881-886.

Rees, J., et al. "Microwave measurement of furnace wall thickness." Trans Inst M C vol. 8, No. 2, Apr.-Jun. 1986. pp. 91-99.

Supplementary European Search Report issued in corresponding European Application No. 12856378 on Aug. 28, 2015.

\* cited by examiner

MICROWAVE PROBE FOR FURNACE REFRACTORY MATERIAL

CROSS REFERENCE TO RELATED APPLICATION

This application is based upon and claims priority from co-pending U.S. Provisional Patent Application Ser. No. 61/567,331 entitled "Microwave Probe for Furnace Refractory Material," filed with the U.S. Patent and Trademark Office on Dec. 6, 2011, by the inventors herein, the specification of which is incorporated herein by reference.

GOVERNMENT LICENSE RIGHTS

This invention was made with Government support under SBIR Phase I Grant No. IIP-1113770 awarded by the National Science Foundation. The Government has certain rights in the invention.

FIELD OF THE INVENTION

This invention relates generally to systems and methods for inspecting the condition of surfaces through measured reflection of transmitted energy, and more particularly to systems and methods for evaluating the condition of refractory materials using microwave radiation.

BACKGROUND OF THE INVENTION

Various industries in the world use large furnaces to melt and hold their product. Example industries are the glass industry and the steel industry. These furnaces may be as large as small buildings. They are constructed using refractory material with very high melting temperatures and good insulation properties (to contain the heat). During operation of these furnaces, the refractory walls of the furnace will degrade. This degradation takes the form of inner surface erosion, stress cracks, and material incursion into the molten material. At this time, there is no well established method of deterministically measuring the thickness of the walls of such furnaces. Because of this, members of the industry must shut down and replace the furnace walls based on estimates of the expected lifetimes of the furnaces. This is an expensive process, and wasteful if done too soon, but dangerous to human life if delayed for too long. The flow of molten glass at such high temperatures inevitably leads to erosion and degradation in the refractory lining and creates a high risk for molten glass leakage through the wall. Once the molten glass leaks through the gaps and cracks in the furnace walls, it causes significant damage to the capital equipment around the furnace and, most importantly, causes significant production disruption. A major leak may require at least 30 days of production disruption before the furnace can be restored to operating mode because it needs to be cooled down, repaired and fired up again.

Another issue is that the refractory material used to build the furnace walls may have defects not visible by surface inspection. The customer purchasing this material would like to have a means for performing internal inspections during the acceptance process from the manufacturer, or the manufacturer would like to have a means for performing internal inspections during manufacture (either to optimize the process, perhaps in real time, or to classify material to be delivered as "without flaws").

Previous efforts have been made to utilize microwaves to detect thickness of materials such as furnace walls, as described for instance in U.S. Pat. No. 6,198,293 to Woskov et al., the specification of which is incorporated herein by reference. However, such prior efforts have met with difficulty. More particularly, while efforts have been made to attempt to determine furnace wall thickness on hot furnaces, those efforts have been generally unsuccessful (it having been discovered by the inventors herein that particularly low frequency bands should be used so as to reduce signal loss and to be able to successfully evaluate the interior condition of such surfaces). Moreover, in placing system components close to the surface to be evaluated, spurious signal reflections have made it quite difficult to isolate what is truly the reflected signal that is of interest, thus further complicating the effort of evaluating the interior condition of such surfaces.

Thus, there remains a need in the art for systems and methods capable of remotely evaluating the condition of such surfaces, such as through reflected microwave measurements, that avoid the problems of such prior art systems.

SUMMARY OF THE INVENTION

Disclosed is a system and method to aid in these inspections that avoid the disadvantages of the prior art. The system and method are operative to take thickness measurements of, and thus evaluate the condition of, materials including but not limited to refractory materials, operating in frequency bands that result in less loss than previously known technologies, and utilizing a system configuration and signal processing techniques that isolate the reflected signal of interest from other spurious antenna reflections, particularly by creating (through the configuration of the antenna assembly) a time delay between such spurious reflections and the actual reflected signal of interest, thus enabling better isolation of the signal of interest. Still further, the antenna assembly is intrinsically matched to the material to be probed, such as by impedance matching the antenna to the particular material (through knowledge of the dielectric and magnetic properties of the material to be evaluated) to even further suppress spurious reflections.

In an exemplary embodiment, microwaves may be used to probe the material. Testing has shown that microwaves may penetrate the material and reflect from the opposite wall and/or from defects. Exemplary microwave devices may measure wall thickness at selected points and/or may scan over an area to permit mapping of the inner wall thickness and shape as well as to form images of defects in the material.

These probes and/or scans may be done on either cold refractory material or hot in-situ material so that flaws and thicknesses may be characterized on either cold material as manufactured or hot material in an operational furnace.

Studies have shown that some types of hot refractory material are microwave frequency dispersive. Thus, the dielectric properties of the material vary with temperature (and thus location). This means that measured wall thickness or flaw location is distorted. Accordingly, an exemplary embodiment may include means for compensation and correction for this property.

In addition to the novel features and advantages mentioned above, other benefits will be readily apparent from the following descriptions of the drawings and exemplary embodiments.

BRIEF DESCRIPTION OF THE DRAWINGS

The numerous advantages of the present invention may be better understood by those skilled in the art by reference to the accompanying figures in which.

DETAILED DESCRIPTION OF THE PREFERRED EMBODIMENTS

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

A basic system in an exemplary embodiment is a short range coherent radar configured to evaluate a remote surface (e.g., the interface between a furnace wall and molten material within the furnace) of a material that is to be evaluated. As used herein, "remote" surface is intended to refer to a surface of a material under evaluation that is opposite the surface immediately adjacent the antenna. Thus, in the case of a furnace, the remote surface comprises the inner surface of the outer wall of the furnace, with the antenna being placed on the outer surface of the outer wall for purposes of carrying out the evaluation.

In an exemplary embodiment, the frequency of the radar is in a band that properly penetrates the material with low enough loss (with respect to the dynamic range) (e.g., typically somewhere between about 1 and 30 GHz, generally, particularly for cold refractory wall analysis). In an exemplary embodiment, the bandwidth of the radar is preferably large enough to permit the depth resolution required by the user (e.g., typically at least about 3 GHz). Moreover, in applications where a hot furnace wall is to be evaluated, the frequency band of the radar should be lower, and particularly less than 10 GHz, preferably less than 8 GHz, and even more preferably less than 5 GHz (where the subject wall surface is very thin, up to 10 GHz would be sufficient), as it has been found that such lower frequency bands reduce loss even in the hot furnace walls that have dielectric characteristics tending to increase loss.

In an exemplary embodiment, the antennas may be designed to be held directly against the surface of the refractory materials. Thus, the antennas may be impedance matched to the refractory material so as to increase the dynamic range of the system by lowering the direct reflections from the antenna-to-material interfaces. By knowing the dielectric and magnetic properties of the material that is to be evaluated, a person of ordinary skill in the art will be able to impedance match the antennas to that particular refractory material. If the system is used on a working furnace, the antennas are preferably also configured of materials that will allow the antennas to tolerate the high temperatures expected. Typically, such antennas may be made of a combination of ceramic and metallic materials.

In one embodiment, the radar is enclosed in a hand held unit. An example may look somewhat like a flashlight. It may measure the thickness of the furnace wall at a single point and record the information in a built-in memory. It also may have a simple display showing thickness of the wall in inches or centimeters. It may be designed to take measurements at multiple locations, storing the data after each test along with time and sequence number. In fact, using well known positioning techniques (e.g., small encoder wheels etc.), it may perform a scan along a line so that probe data as a function of position may be collected. It may then transform the set of probe data to a 1-dimensional depth profile using imaging techniques (to be discussed later).

In another embodiment, the radar may use an array of antennas to measure the data at an array of points. It may operate as a MIMO (multiple input, multiple output) radar. An example of the system may include a set of switches so that the transmit and receive antennas may be switched over the elements of the antenna array. Data processing may be used to form images or maps of the inner surface of the furnace wall. Maps of thickness versus position may be provided. An example of the antenna may be hand-placed, and the radar and signal processing may be interfaced over a flexible cable.

In yet another embodiment, the radar may be designed to scan the antennas over a block of refractory material to look for defects. In this example, the data point spacing may be less than ¼ wavelength at the highest frequency of operation. The signal processing may be designed to form three dimensional images of defects in blocks of refractory material as manufactured. Computer software may be used to classify the defects as serious or not serious and to classify the block of refractory material as acceptable or not acceptable for use in the furnace.

In exemplary embodiments, the radar system may be as portable as possible and as a user may desire. An example of the single point device may be the size of a flashlight. The furnace scanning system may be enclosed in a portable box with a hand held antenna array on a cable. The refractory block scanning system may be a transportable system that may be transported to the test site and set up for scanning In each of the embodiments envisaged, the antennas are provided a physical configuration that creates a time delay between spurious reflections and the actual reflected signal of interest, thus enabling better isolation of the signal of interest. More particularly, the antennae used herein may include waveguide horns that lengthen the size of the radar head. While any transmitting antenna will cause a receiving antenna to receive unwanted, spurious radiation that has been reflected off of the near, outer surface of the material under analysis, and while coupling between transmitting and receiving antennas will cause the receiving antenna to likewise receive unwanted, spurious radiation, the extended length of the antenna assembly will cause a time delay between the spurious radiation detected by the receiving antenna and the actual radiation of interest that is reflected off of the remote surface of the material under analysis. Preferably, such time delay should be at least 3-5 nanoseconds ("ns"), so that received reflected radiation may be identified as being reflected from a particular source based upon the time between its reception and a temporally adjacent signal reception. This, in turn, allows the analyzing software (discussed below) to distinguish, for a given transmission or microwave energy, spuriously reflected radiation (reflected or produced by sources not of interest) from radiation actually reflected by the surface under analysis. Those of ordinary skill in the art will be able to determine a specific dimension for the length of such antenna assembly in order to maintain such a time delay for a given application, it being noted, however, that a tradeoff will exist between increasing size of the antennas and physical space on and surrounding the surface that is to be analyzed.

Likewise, in each of the embodiments envisaged, the antennas are, as discussed elsewhere in this specification, impedance matched to the material under analysis, which further helps to suppress spurious reflections.

Details of an Exemplary Embodiment

Figure 1:
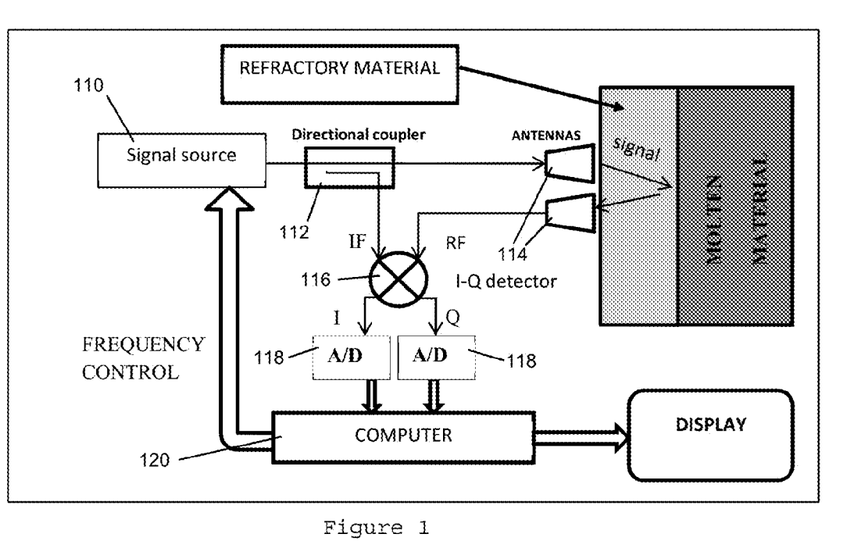
FIG. 1 is schematic view of an exemplary embodiment of a bistatic single point coherent radar probe. In this example, amplifiers and filters are not shown for clarity. An example of an actual radar may, for example, be the size of a flashlight.

The details of one exemplary embodiment are shown in FIG. 1, and further detailed below.

1. Signal source 110: This is an example of a tunable signal source where the tuning is controlled by the computer. It may be any version of such a device (voltage controlled oscillator, frequency synthesizer, etc.).

2. Directional coupler 112: In this example, the directional coupler picks off a small component of the original RF signal and is used to provide the coherent detector (I/Q mixer) with a reference signal (e.g., a phase coherent copy of the transmitted signal).

3. Transmit and receive antennas 114: These exemplary antennas are:
   a. wide band enough to cover the operational frequency band;
   b. able to tolerate the required temperature range;
   c. preferably impedance matched to the refractory material;
   d. with low cross-coupling;
   e. with stabile or known polarization characteristics (linear polarization or circular polarization); and
   f. preferably having a small physical size.

4. Coherent detector 116: In this example, shown as an I/Q detector (a device that outputs voltages proportional to the in-phase and quadrature-phase components of the received RF signal relative to the reference IF signal; thus permitting both amplitude and relative phase to be measured).

5. Analog to digital converters 118: In this exemplary embodiment, these devices output digital data proportional to the I and Q voltages output by the I/Q mixer (or other coherent detector system), as input to the computer system.

6. Computer system 120: In this example, the computer system reads the digital data from the coherent detectors and also controls the frequency of the signal source. It is further adapted to display the results to the user.

7. Computer software (executed by computer 120): This example of computer software is adapted to perform the following functions:
   a. reads the coherent radar data;
   b. performs calibration and correction for signal dispersion (due to the antenna characteristics and/or the refractory material);
   c. computes the thickness of the refractory material based on the reflection time (or other characteristics) of the RF signals;
   d. formats and displays the data in a user-friendly way; and
   e. stores the data for further off-site processing and analysis.

Figure 9:
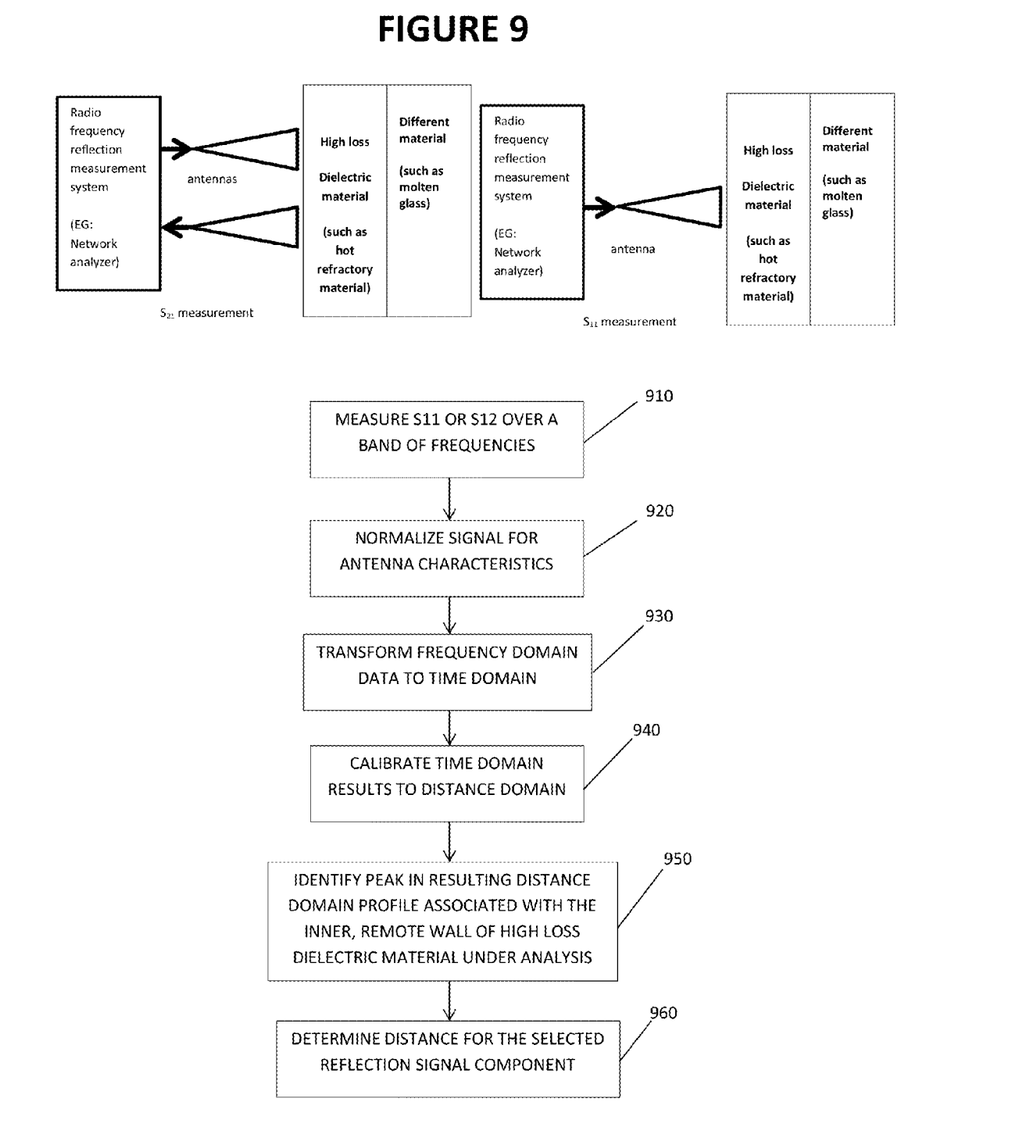
FIG. 9 shows a schematic view of a method for computing the thickness of a high loss dielectric material according to embodiments of the invention.

In this embodiment, and in fact with regard to each of the embodiments envisaged, computing the thickness of the subject high loss dielectric material, such as refractory material, may be carried out through the methods depicted in FIG. 9. At step 910, $S_{11}$ or $S_{21}$ (depending upon whether a monostatic or bistatic configuration is used) is measured over a band of frequency (coherent radar scattering (complex numbers)). This is a high dynamic range data set (>90 dB). There are many ways that this may be accomplished as will be apparent to those of ordinary skill in the art, such as through use of a network analyzer. Next, at step 920 (and as an optional step), the signal may be normalized for the antenna characteristics (to remove antenna frequency characteristics (dispersion)). The antenna characteristics can be determined, by way of non-limiting example, by measuring the reflection from a reference (e.g., a known characteristic and thickness) block of similar high loss dielectric material, through processes well known to those skilled in the art. Next, at step 930, the frequency domain data is transformed to the time domain, typically through performing an inverse Fourier transform. Alternatively, a number of model-based inverse spectral transforms could likewise be used. Next, at step 940, the time domain results are calibrated to the distance domain by using the known velocity of the radio frequency signal in the high loss dielectric material. Next, at step 950, the peak is identified in the resulting distance domain profile associated with the reflection from the interface with the inner, remote wall of the high loss dielectric material under analysis. Last, at step 960, the distance for the selected reflection signal component is determined, which is related to the thickness of the high loss dielectric. Delay time (distance) associated with the antennas and cables is subtracted in order to produce the ultimate final thickness determination.

Referring again to FIG. 1, it is noted that some amplifiers and filters have been left off to simplify the explanation. The components not shown are not critical to the explanation of the invention.

Likewise, note that with regard to the exemplary embodiment of FIG. 1, there is no radar pulse or timing signals. In this embodiment, the radar is not a pulse radar because the radar reflection time is too short (less than a few nanoseconds) for typical switching systems. This means that the transmit signal leakage and direct coupling terms are preferably removed by signal processing rather than hardware switches. Therefore, the dynamic range of this embodiment of the overall system is high enough so that such signal processing may be done.

Figure 2:
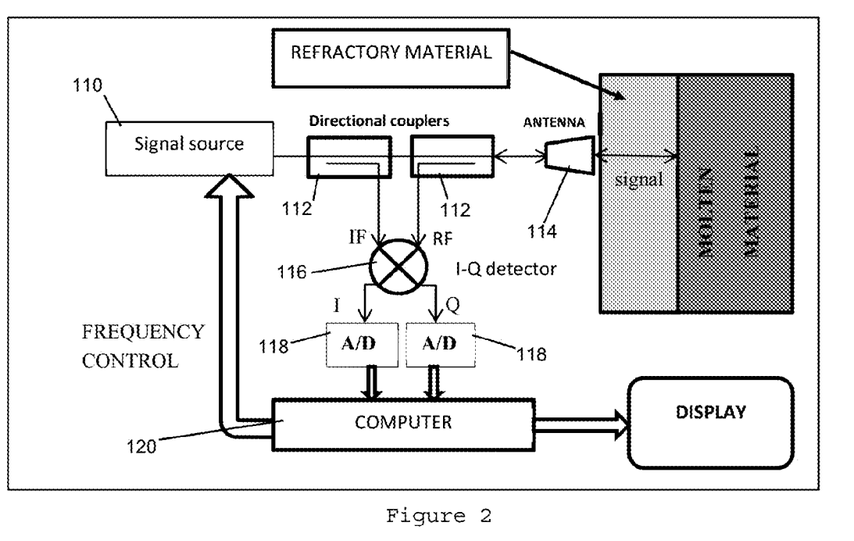
FIG. 2 is a schematic view of an exemplary embodiment of a monostatic single point coherent radar probe. Amplifiers and filters are not shown for clarity.

In FIG. 2, an exemplary embodiment using a single antenna 114 is shown. This is a monostatic system. In this example, the reflected signal returns to the antenna 114 along the same path as the transmitted signal. There are a number of physical and data analysis reasons why this may be preferred in some exemplary embodiments.

The only differences between the examples in FIGS. 1 and 2 are the use of only a single antenna 114 in FIG. 2 and the use of two directional couplers 112 in FIG. 2.

Imaging Concepts

In an exemplary embodiment, a coherent radar (as shown in FIGS. 1 and 2 or as configured in some other way) is mechanically or electrically scanned over the region of interest to create a three dimensional image of the inner walls and/or imbedded flaws in the refractory material.

Figure 3:
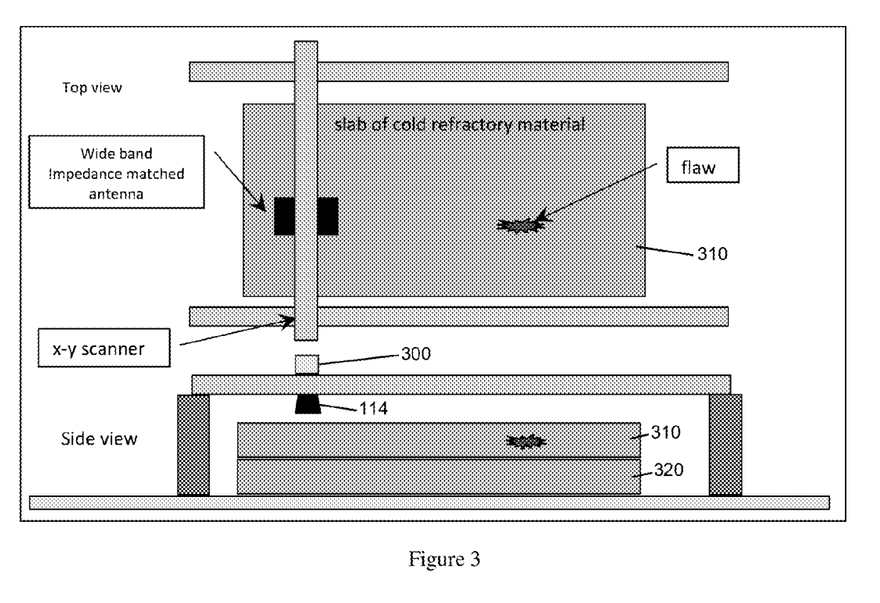
FIG. 3 is a schematic view of an exemplary scanner in use to image the internal flaws in a slab of refractory material.

An example of a scanning method and apparatus is shown in FIG. 3. As exemplified in FIG. 3, an x-y scanner (shown generally at 300) is used to permit the coherent radar (or just the radar antennas connected by flexible cables) to scan the surface of a slab of cold refractory material. A computer controls the movement of the x-y scanner 300 so that the radar antennas 114 may move in an x-y pattern to scan the cold refractory material 310. As an example, this slab of cold refractory material may be as purchased new from a supplier, and the testing may be done to determine the existence, characteristic (size/shape, voids and/or cracks, etc.), and/or location of flaws in the material. For purposes of explanation, the use of the word "cold" in these descriptions is meant to mean "not heated to operational furnace temperatures."

In an exemplary embodiment, the process of scanning may involve moving the radar antennas 114 over the region of interest with an x-y grid spacing small enough to avoid aliasing. At each grid point, a coherent radar scan in frequency may be taken. The domain of the scan may be set to cover the area of interest (often the entire slab 310). The spatial increment of the scan may be sufficiently small so as to avoid spatial aliasing. Typically, this spacing may thus be ¼ wavelength at the shortest wavelength used in the scan. The RF attenuation is less in cold refractory material than in material at operational furnace temperatures.

Note that in the exemplary set-up shown in FIG. 3, the refractory material under test is sitting on a slab of similar refractory material 320 (pre-determined to have no flaws). This may permit the coherent radar to image the flaws without a strong reflecting surface at the bottom layer of the refractory material under test. This technique may improve the dynamic range of the coherent radar.

Figure 4:
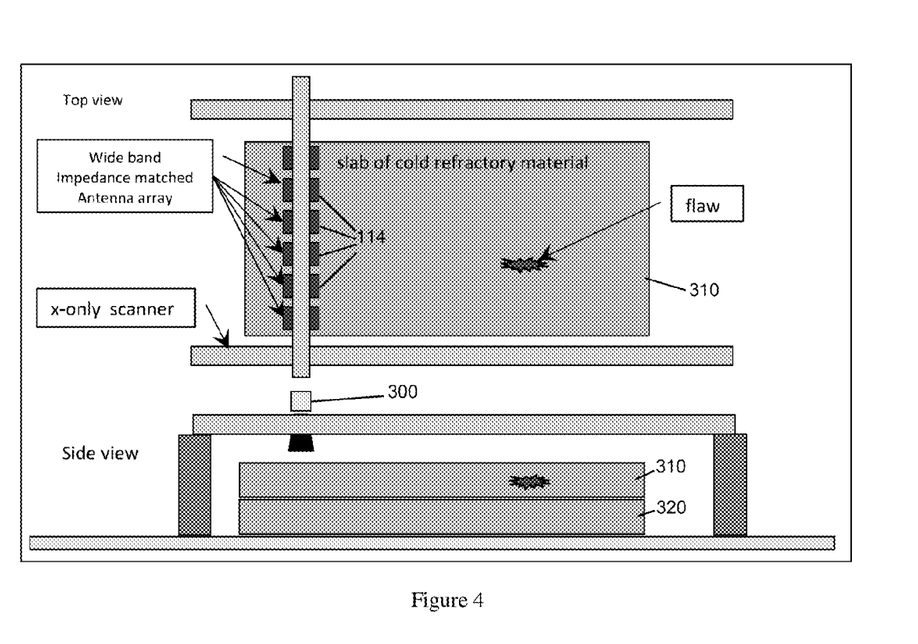
FIG. 4 is a schematic view of an exemplary array of antennas as part of the scanning system. In this exemplary embodiment, the antennas (or antenna pairs) may be switched in sequence to permit scanning in the y-direction, and the scanner moves the array in the x-direction in order to achieve the other dimension.

It is also possible to have an array of antennas 114. An example of such a system is shown in FIG. 4. In this figure, a linear array of antennas 114 is switched to scan in one direction, and the mechanical system permits scanning this array in the other direction.

Another possibility is the use of a fully electronically switched array of antennas 114. As shown in the example of FIG. 5, this may permit the slab 310 to be scanned electronically and thus such a system may have no moving antenna parts.

Figure 5:
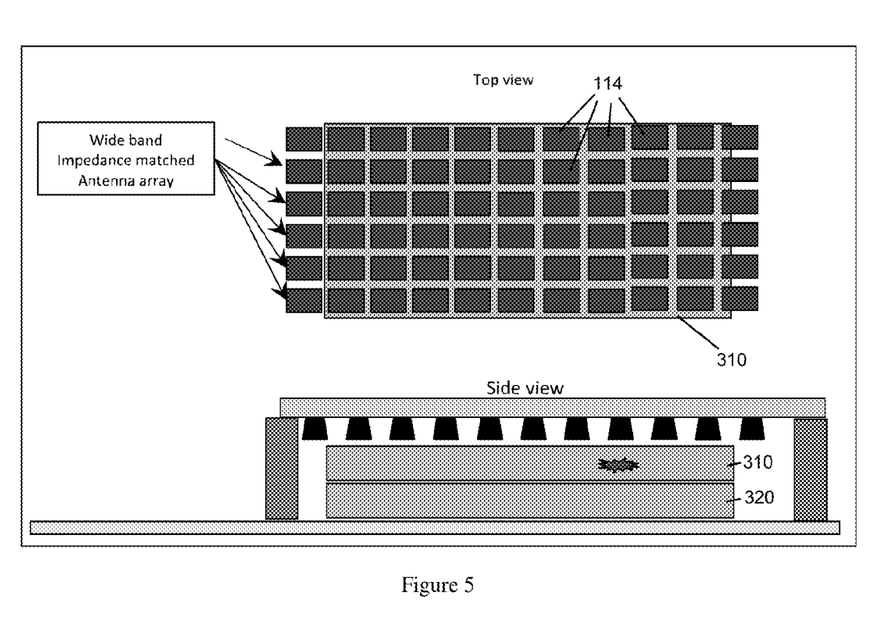
FIG. 5 is a schematic view of an exemplary switched array used to scan for a flaw in a slab.

As shown in FIG. 5, an array of switched coherent-radar antennas 114 may be used to scan the slab 310 for imbedded flaws. It is also possible to have an array of radar "front-ends" used in this example. For example, as well as an array of switched antennas 114, it is also possible to include a coherent detector at each receive antenna 114 so that the received data may be obtained rapidly and delivered to the computer system for further processing. Note that the array system may be operated as a MIMO (multiple input, multiple output) radar by transmitting on one of the elements while receiving data from all of the other elements, and then shifting the assignment (location) of the transmitting element.

Figure 6:
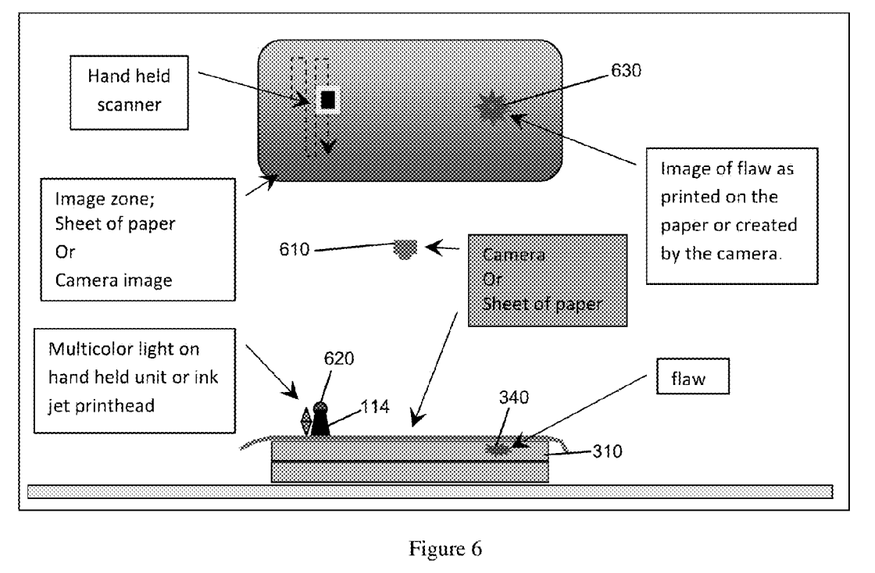
FIG. 6 is a schematic view of an exemplary hand-held scanner. In this exemplary embodiment, tracking may be accomplished by an overhead camera or simply a sheet of RF transparent material (such as paper).

An exemplary embodiment of the system may be portable such that it may be transported as individual components and set up at the test site. In an exemplary embodiment, the scanner or the array system may be assembled quickly on-site. In order to provide maximum portability, it may be possible to develop a hand-held unit that may be scanned by hand over the refractory slab. With reference to FIG. 6, a transportable data mapping technique may involve using an overhead camera 610 to record the location and color of a light 620 on the top of the hand held scanner 114. In this way, an image of the block itself and the light color over the domain of the slab may be obtained. For example, the color of the light may be proportional to the characteristic of the flaw (depth, size, etc.). An alternative technique may attach a sheet of thin RF-transparent material (such as paper) to the refractory slab 310, and then scan over the slab/paper with a hand-held unit. In this embodiment, the hand held unit may incorporate a printer (e.g., multi-color ink-jet) so that an image 630 of the internal structure of the slab may be transferred to the paper. In this embodiment, the color of the ink deposited on the paper may be proportional to the characteristics of the flaw 340 (depth, size, etc.). Another embodiment may include a small hand-emplaced MIMO array adapted to create an internal image of a sub-section of the slab under test. In this example, a relatively small number of MIMO array positions may permit the entire slab 310 to be internally mapped. Image data in the computer may be "stitched" together to form the entire slab image.

It may also be important to be able to form a 3-D image of the inner wall shape of an operating furnace. This furnace wall will be very hot, and the inner surface will be in contact with the product (such as molten glass, iron, or steel). The inner surface will be distorted by variations in the erosion rate along the inner surface of the furnace. It may be important to be able to characterize this inner surface shape. For this reason, a high temperature array of antennas may be used. In an exemplary embodiment, this array of antennas may be placed against the outer wall of the furnace so as to be able to form a radar image of the inner surface of the wall. In this embodiment, the antenna array is adapted to survive the high temperatures of the outer surface of the furnace wall. This example of the array may be conformal to the outer surface of the wall and not be so large as to be impossible to position on the outer surface because of outer surface structures such as support beams that may be used to support the refractory material that make up the walls.

Experimental Concept Testing

A concept testing used laboratory equipment to probe through various thicknesses of refractory material. An example of such a test is shown in FIG. 7.

Figure 7:
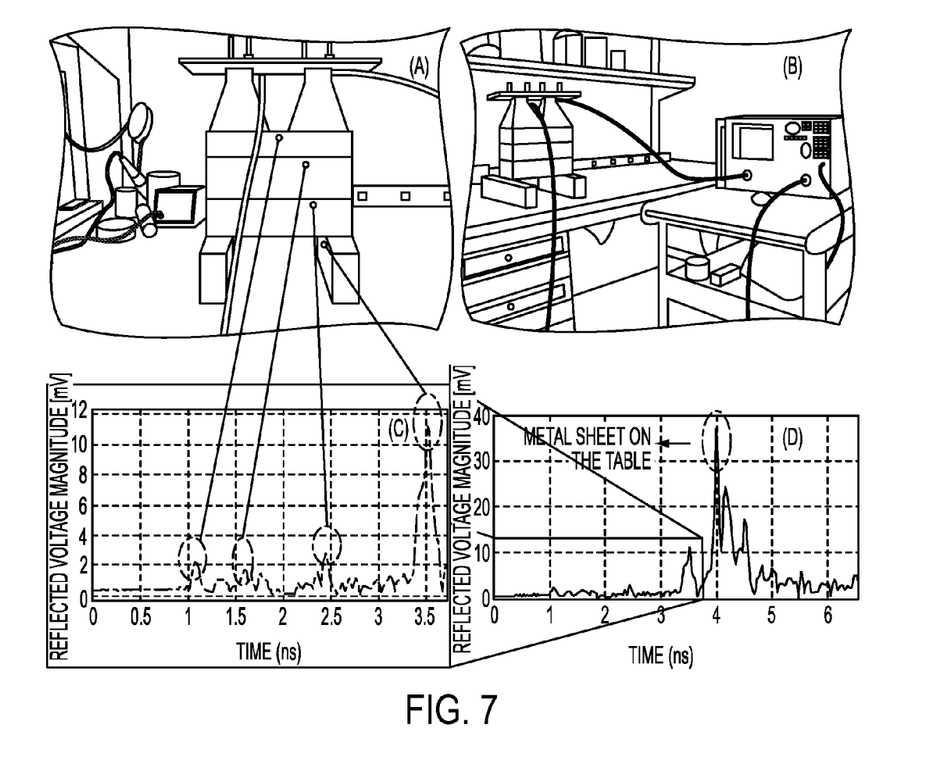
FIG. 7 shows an example of refractory material testing (in this case, AZS): (A) a photo of an example of multiple slabs with wide band ridged waveguide horns used for bistatic probing; (B) a photo of an example of connections to a Network Analyzer; (C) an example of a plot of early time domain results as a function of time in nanoseconds showing returns from refractory slab gaps, where the bottom refractory-to-air interface can also be seen; and (D) an example of a plot of an extension to 6.5 ns so that time domain reflection terms from the metal sheet on the table can be seen.

Early tests as exemplified in FIG. 7 showed that it is very practical to use a wide band radar to penetrate cold refractory material in the radar band from 1 to 12 GHz, and to transform the coherent radar data to the time domain (using a well-known inverse Fourier transform).

Figure 8:
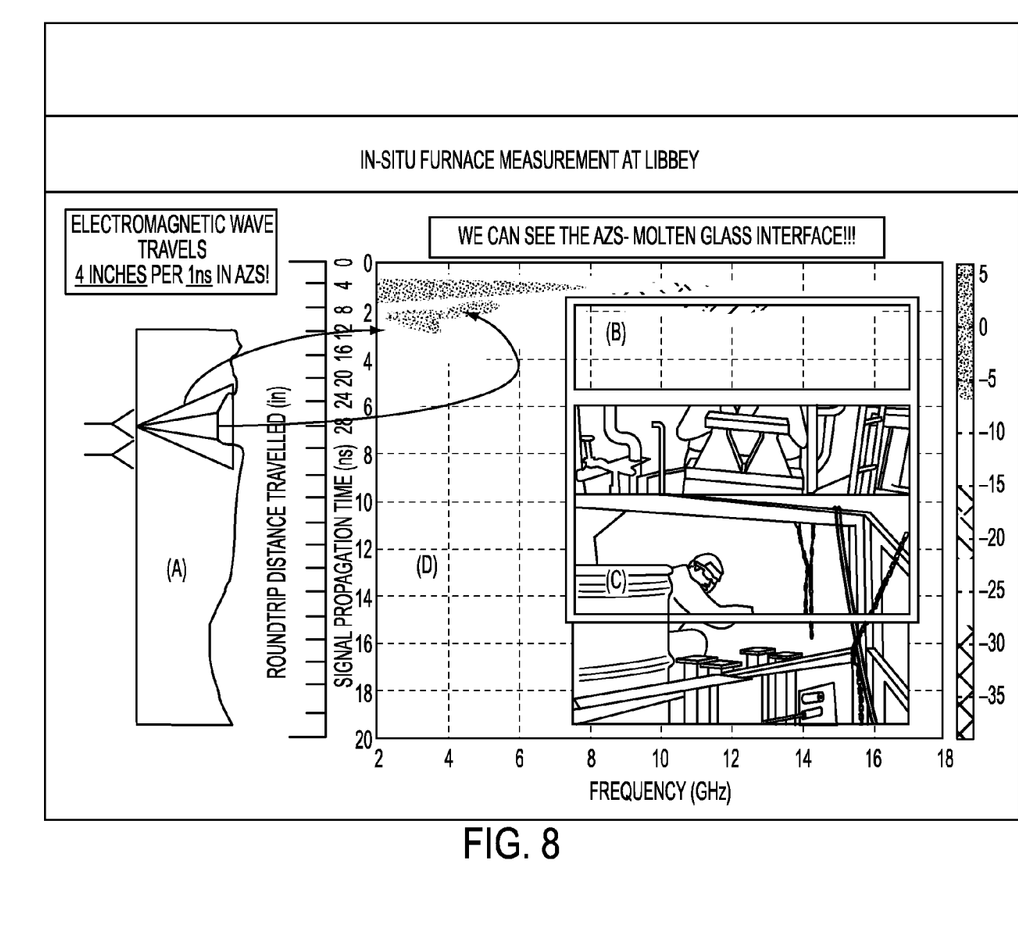
FIG. 8 shows an example of testing results at a large molten glass furnace facility: (A) a schematic sketch of geometry of an exemplary embodiment; (B) a photo of an example of antennas used for testing; (C) a photo of an example of antennas being held against the exterior furnace wall (Network Analyzer not shown); and (D) an example of a plot of time delay versus frequency extracted from analysis of coherent radar data.

Note in FIG. 8 that there are several response terms:
1. Horn-to-horn coupling; 2 to 9 GHz; 1 ns.
2. Closer wall term; 3 to 6 GHz; 2 ns
3. Farther wall term; 2 to 3.5 GHz; 3 ns.

In this test, the refractory material (AZS) has a dielectric constant of approximately 9 and thus a velocity of propagation 3 times slower than that of free space. Since free space velocity is 12 inches per ns (nanosecond), the velocity in this refractory material is 4 inches per ns. Radar is a two-way reflection, so the thickness of the wall is equal to the time delay in ns multiplied by 2 inches. The close wall term is 1 ns farther than the direct coupling term, and thus represents a wall region that is only 2 inches thick. The farther wall term is 2 ns farther than the direct coupling term and thus represents a wall region that is 4 inches thick.

A careful study of this set of data showed that the refractory material is electromagnetically dispersive. Thus, the dielectric constant and thus the velocity of propagation of the electromagnetic waves in the material vary as a function of temperature and microwave frequency. Accordingly, in an exemplary embodiment, the wall thickness estimations and the internal flaw mapping algorithms may take the dispersive nature of the hot refractory material into account during the data processing.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain some of the principles of the present invention so that others skilled in the art may practice the invention. Having shown and described exemplary embodiments of the present invention, those skilled in the art will realize that many variations and modifications may be made to affect the described invention. For example, while the above discussion is focused on the evaluation of a furnace wall, the principles set forth herein may likewise apply to any high loss dielectric material, including (by way of example and not by way of limitation) furnace refractory material, soil, wet concrete, wet sand, human flesh, animal flesh, various liquids, etc. Those of ordinary skill in the radar arts will be able to configure the inventive system and method described herein to their specific application without departing from the spirit and scope of the instant invention.

Many of those variations and modifications will provide the same result and fall within the spirit of the claimed invention. It is the intention, therefore, to limit the invention only as indicated by the scope of the claims.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

We claim:

1. A method for evaluating a condition of a remote surface of a material, comprising the steps of:
    providing a wide band coherent radar antenna that is selected based upon an impedance match with the material to be evaluated, wherein said antenna is provided a physical configuration adapted to delay receipt of a signal of interest reflected from said remote surface of said material by a time period sufficient to distinguish between said reflected signal of interest and reflected spurious signals from a near surface of said material;
    placing said antenna adjacent said near surface of said material;
    irradiating said material with coherent microwave radiation tuned over a frequency range;
    detecting reflected microwave radiation from said remote surface of said material; and
    determining a thickness of the material based upon a determined distance traveled by said signal of interest.

2. The method of claim 1, wherein said distance traveled by said signal of interest is determined based upon a time of travel of said signal of interest.

3. The method of claim 2, wherein the time of travel of said signal of interest is greater than a time of travel of said spurious signals by a sufficient extent so as to enable temporal isolation of said signal of interest from said spurious signals.

4. The method of claim 1, wherein said step of determining the thickness of the material further comprises the steps of:
    measuring coherent radar scattering from said reflected microwave radiation to produce frequency domain data;
    transforming said frequency domain data to time domain data;
    calibrating said time domain data to a distance domain profile;
    identifying a peak in said distance domain profile associated with said reflected microwave radiation from said remote surface of said material;
    determining a distance traveled by said reflected microwave radiation from said remote surface of said material; and
    displaying a thickness measurement of said material based upon said distance traveled by said reflected microwave radiation from said remote surface of said material.

5. The method of claim 4, wherein said step of calibrating said time domain data to a distance domain profile is performed based upon a known velocity of a radio frequency signal travelling through said material.

6. The method of claim 4, further comprising the step of subtracting a delay time attributable to said antenna and cables extending from said antenna to processing equipment.

7. The method of claim 1, wherein said antenna is formed as a single hand-held unit.

8. The method of claim 1, further comprising the step of generating a 3-dimensional image of said remote surface of said material.

9. The method of claim 1, further comprising the step of scanning one or more of said antenna in a pattern over said material.

10. The method of claim 1, wherein said frequency range is between 1 and 30 GHz.

11. The method of claim 10, wherein said frequency range is between 1 and 8 GHz.

12. The method of claim 11, wherein said frequency range is between 1 and 5 GHz.

13. A system for evaluating the condition of a remote surface of a material, comprising:
    a wide band coherent radar antenna that is selected based upon an impedance match with the material to be evaluated, wherein said antenna is provided a physical configuration adapted to delay receipt of a signal of interest reflected from said remote surface of said material by a time period sufficient to distinguish between said reflected signal of interest and reflected spurious signals from a near surface of said material; and
    a computer processor having executable computer code configured to:
        measure coherent radar scattering from reflected microwave radiation to produce frequency domain data;
        transform said frequency domain data to time domain data;
        calibrate said time domain data to a distance domain profile;

identify a peak in said distance domain profile associated with said reflected microwave radiation from said remote surface of said material;

determine a distance traveled by said reflected microwave radiation from said remote surface of said material; and display a thickness measurement of said material based upon said distance traveled by said reflected microwave radiation from said remote surface of said material.

14. The system of claim 13, wherein calibrating said time domain data to a distance domain profile is performed by said computer executable code based upon a known velocity of a radio frequency signal travelling through said material.

15. The system of claim 13, wherein said antenna is formed as a single hand-held unit.

16. The system of claim 13, wherein said executable computer code is further configured to generate a 3-dimensional image of said remote surface of said material.

17. The system of claim 13, wherein the system is adapted to operate over a frequency range of between 1 and 30 GHz.

18. The system of claim 17, wherein the system is adapted to operate over a frequency range of between 1 and 8 GHz.

19. The system of claim 18, wherein the system is adapted to operate over a frequency range of between 1 and 5 GHz.

* * * * *